United States Patent [19]

Hanna

[11] 4,429,696
[45] Feb. 7, 1984

[54] SURGICAL APPARATUS FOR PRECISELY CUTTING OUT THE CORNEA

[75] Inventor: Khalil Hanna, Paris, France

[73] Assignee: Sevifra S.A., Paris, France

[21] Appl. No.: 285,684

[22] Filed: Jul. 21, 1981

[30] Foreign Application Priority Data

May 11, 1981 [EP] European Pat. Off. ........ 81400745.6
Sep. 3, 1980 [FR] France .................................. 80 19014

[51] Int. Cl.³ ............................................. A61B 17/32
[52] U.S. Cl. ..................................... 128/310; 128/305
[58] Field of Search ...................... 128/305, 305.1, 310, 128/753, 754; 408/703

[56] References Cited

U.S. PATENT DOCUMENTS

| 2,838,050 | 6/1958 | Ara ...................... 128/310 |
| 3,074,407 | 1/1963 | Moon et al. .................... 128/310 X |
| 4,205,682 | 6/1980 | Crock et al. ......................... 128/305 |
| 4,236,519 | 12/1980 | La Russa et al. ..................... 128/305 |
| 4,336,805 | 6/1982 | Smirmaul ........................ 128/305 X |

FOREIGN PATENT DOCUMENTS 192351 2/1967 U.S.S.R. .............................. 128/305

Primary Examiner—Michael H. Thaler
Attorney, Agent, or Firm—Alan H. Levine

[57] ABSTRACT

The present invention concerns a trephine for making at least one circular incision on the cornea of an eye. The trephine comprises an external support forming a casing and having a base portion for applying it to the eye, an internal blade carrier which is movable in the support, and a drive mechanism for driving the blade carrier with respect to the support. The blade carrier is driven by the drive mechanism which cause it to screw into and out of the support and the blade is cylindrical, the cutting blade portion being formed by its lower circular edge.

34 Claims, 14 Drawing Figures

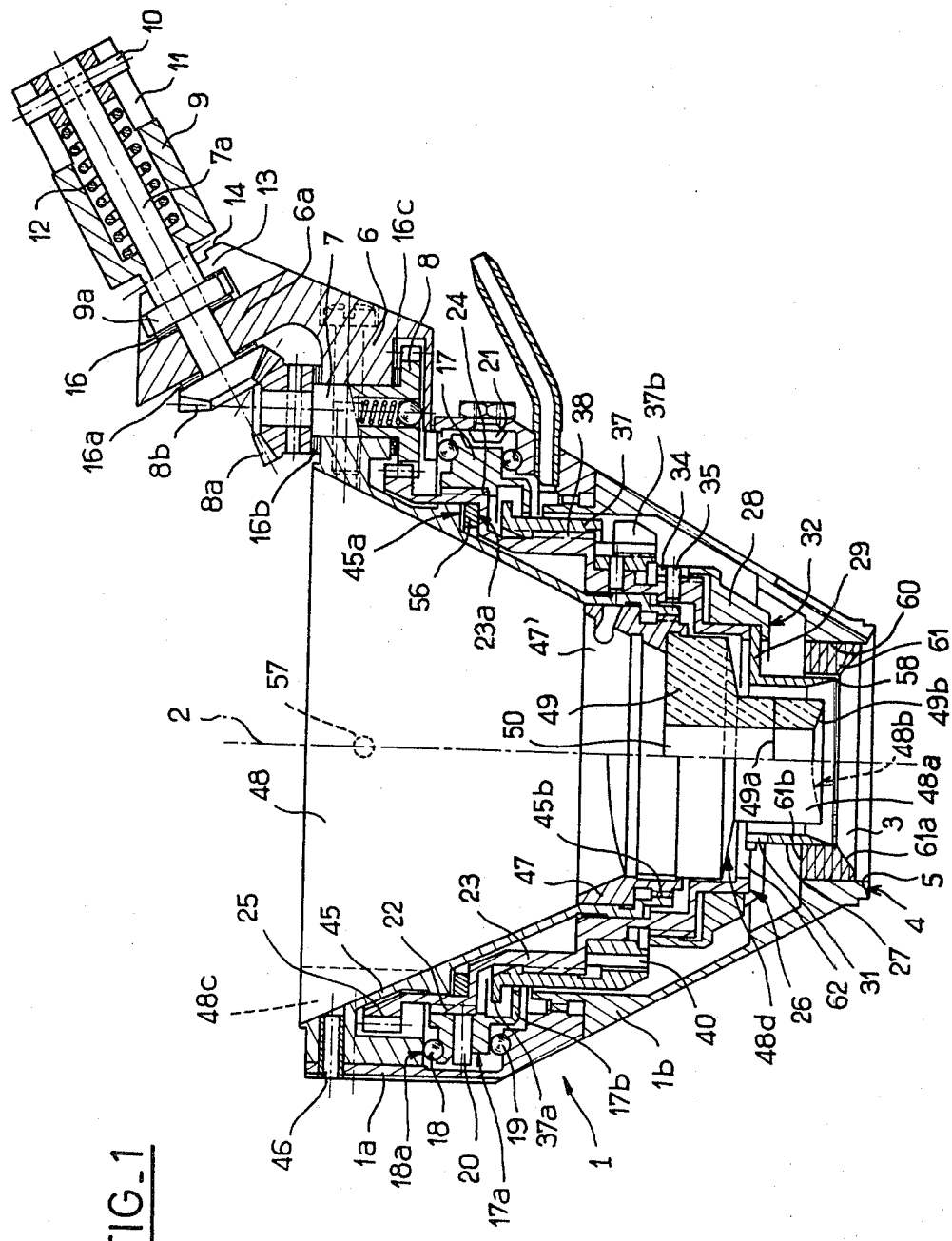
FIG_1

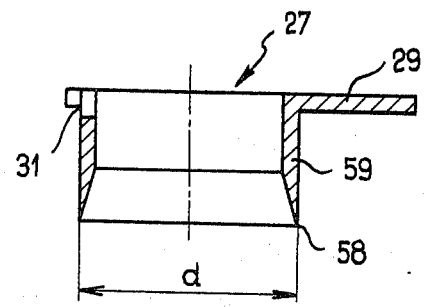
FIG_2
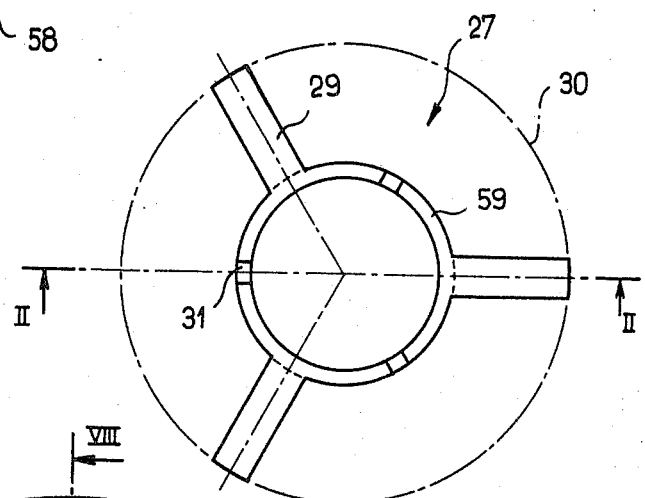
FIG_3
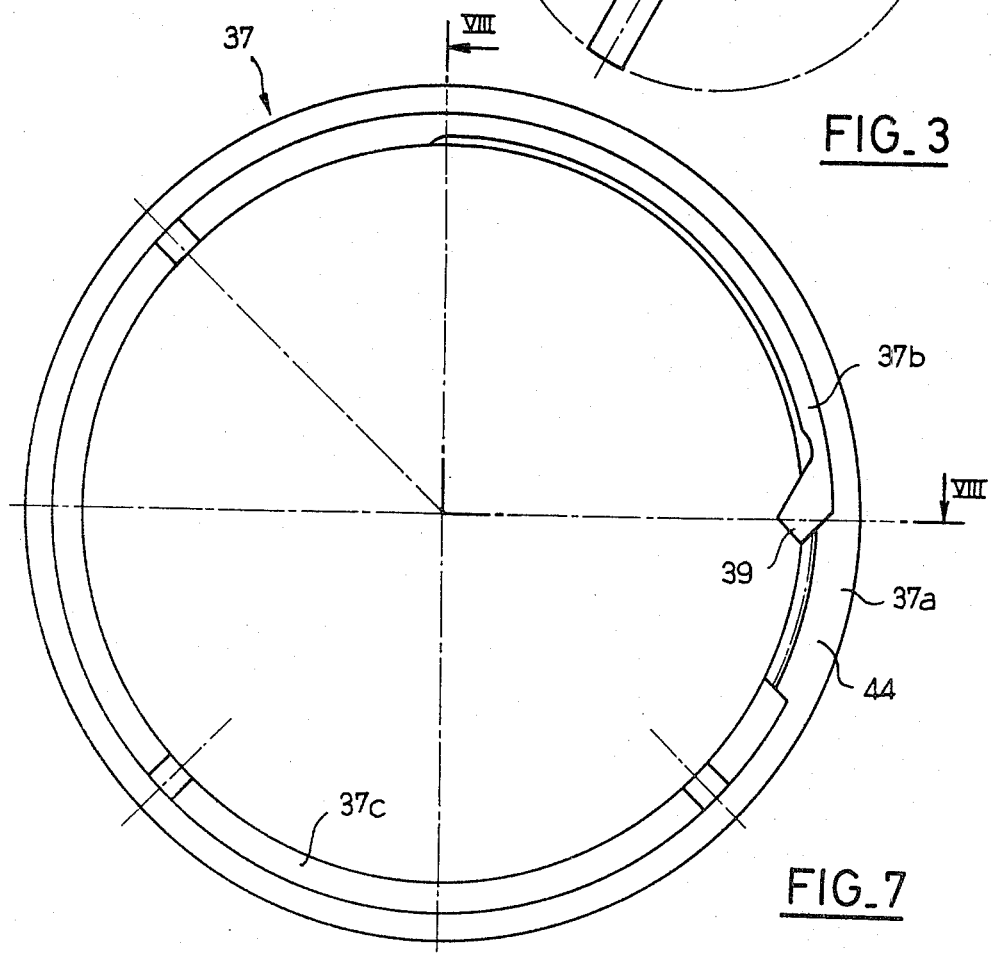
FIG_7

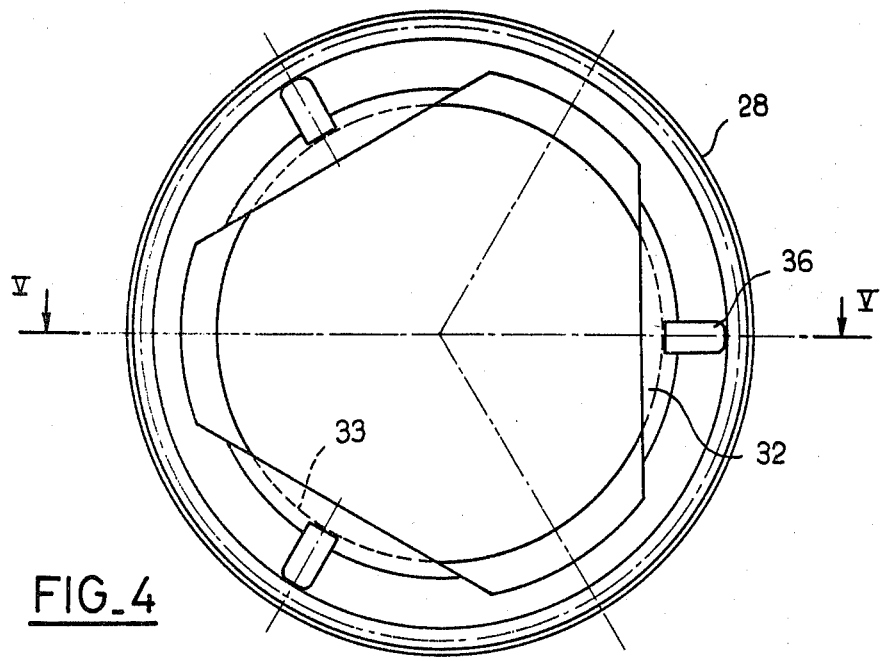
FIG_4
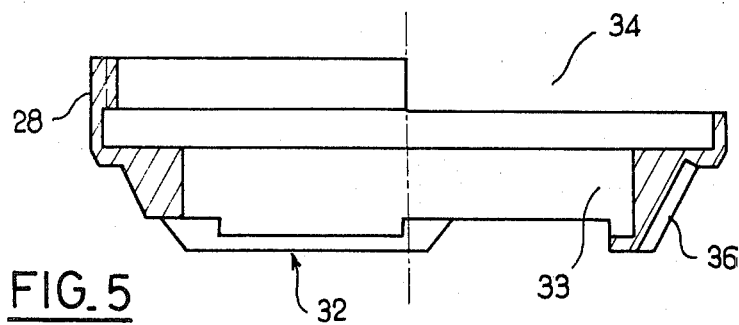
FIG_5
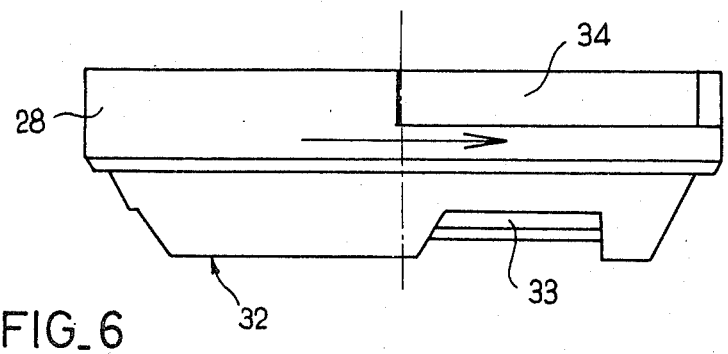
FIG_6

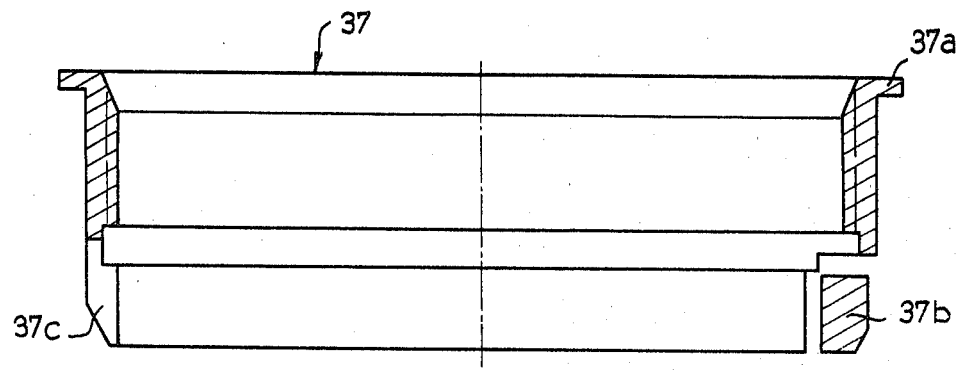
FIG_8
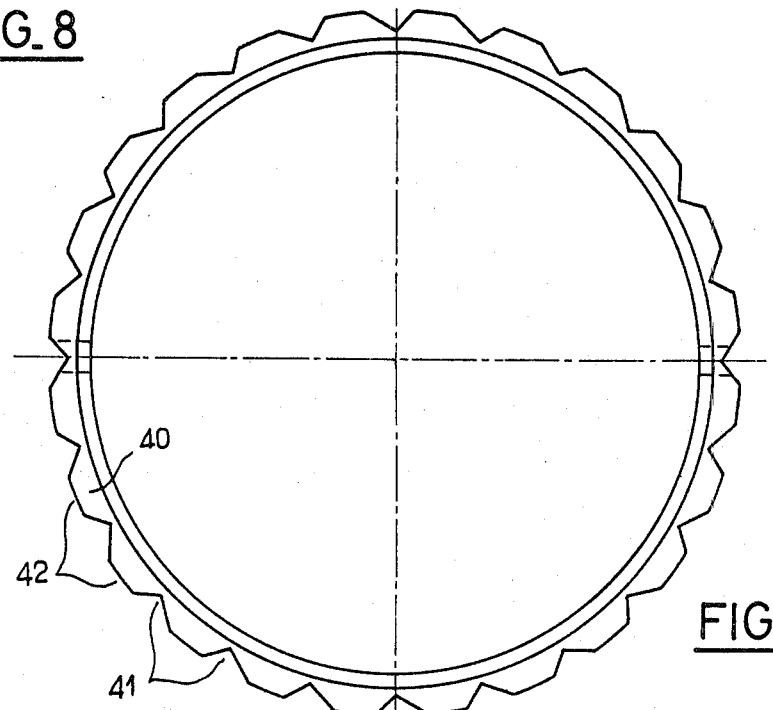
FIG_9
FIG_10
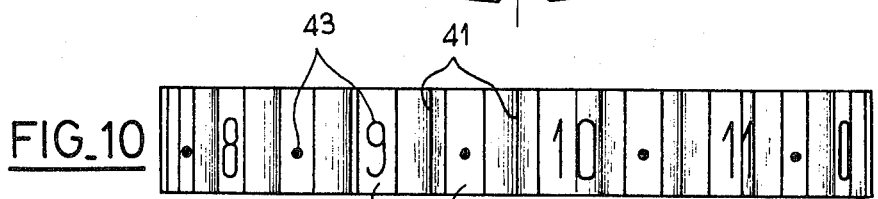
FIG_11
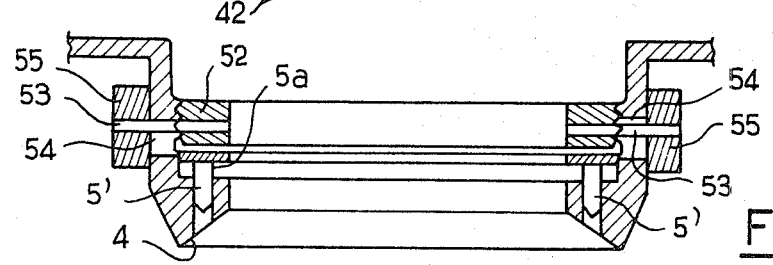

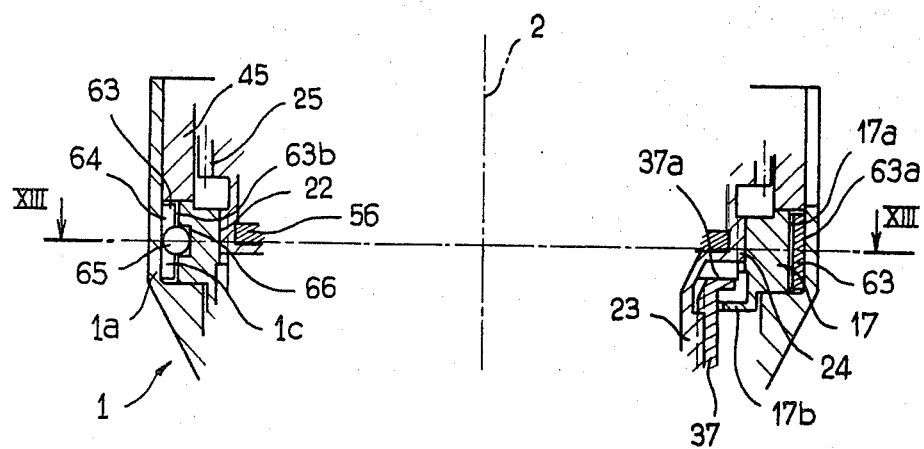
FIG_12
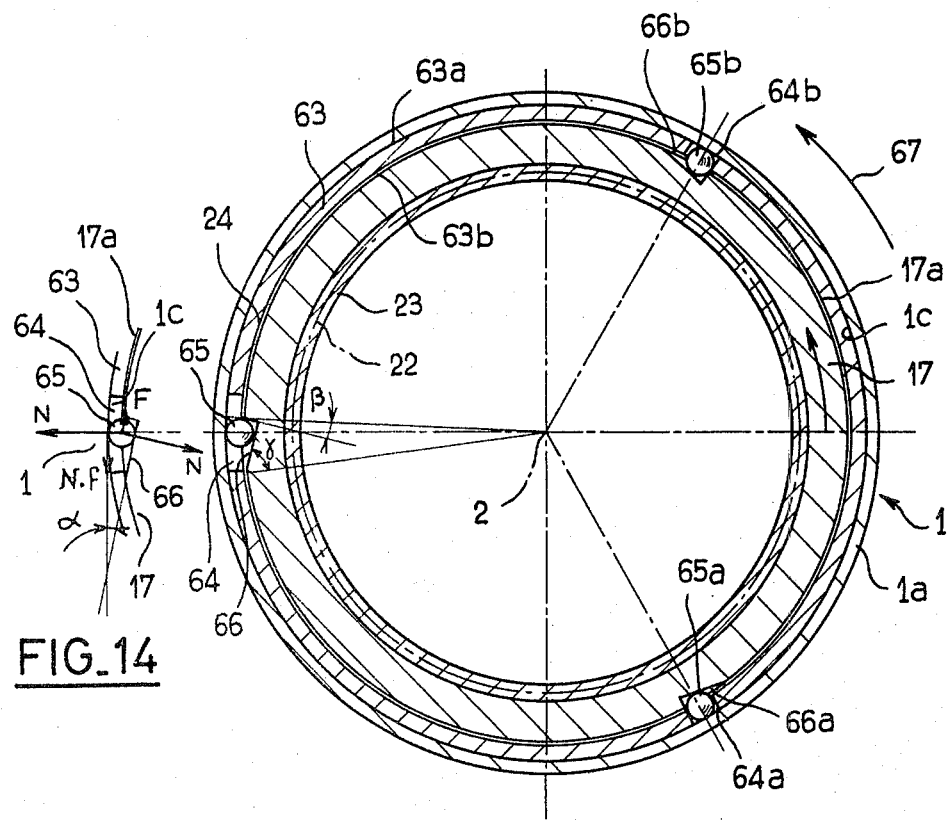
FIG_14
FIG_13

SURGICAL APPARATUS FOR PRECISELY CUTTING OUT THE CORNEA

BACKGROUND OF THE INVENTION

The present invention concerns a surgical apparatus or "trephine" for precisely cutting out the cornea.

Keratoplasty requires the removal of the cornea portion of the eye affected, to replace it by a graft, that is to say a healthy cornea portion.

In order to carry out the removal operation, a generally circular incision is first made around the affected portion. The incised portion is then withdrawn in known manner. These operations are carried out under a microscope as they require a very high degree of precision and the lateral incision or cut is made by means of an apparatus referred to as a trephine.

Such trephines are also used in refractive surgery in order to make a circular incision on the cornea whereby, by controlling the stitching, it is possible to apply to the cornea stresses which result in a modification of the curvature thereof.

The invention concerns a novel apparatus of the trephine type.

At the present time, there are two main types of apparatus in existence. The first comprises a cutting instrument with a cylindrical blade, the circular cutting portion of which is applied to the eye and performs a rotary movement to make the incision. The depth of the incision is controlled by an internal buffer member which is spaced axially at a greater or lesser distance from the cutting edge and which bears on the part of the cornea which is within the incision. This apparatus is very delicate in its handling, as it is not retained on the eye and may slip or take up an inclined position. For this reason, the incision is not precise in depth and the depth of the incision may be uneven if, during the operation, the apparatus has taken up an inclined position.

The second type of the known apparatuses comprises a laterally cutting and pointed blade which is fixed in an axially adjustable manner to a support member which is supported on the eye, outside the line of the incision, and an internal transparent lens around which the blade may be rotated. In this case, the incision is made progressively by an alternate succession of rotary movements and penetrating movements of the blade. If the apparatus moves relative to the eye during the making of the incision, it may not be possible to achieve a condition of coincidence between the point at which the blade started cutting and the point at which it arrives after the rotational movement thereof. In that case, the incision has to be finished manually and the shape of the cut-out portion is no longer regular.

SUMMARY OF THE INVENTION

With the present invention, it is possible on the one hand to make a perfectly circular incision which is precise and equal in depth over its entire perimeter, with adjustment before the apparatus is placed on the eye, with the cutter in a retracted condition, and on the other hand, better to secure the apparatus on the eye. In particular, the trephine according to the invention makes it possible to make at least two concentric incisions on the cornea, with or without removal of the intermediate annular portion, to modify the curvature of the cornea; by virtue of its circular blade, the trephine of the invention also makes it possible to remove a conserved graft.

Therefore, for this purpose, the present invention concerns a trephine intended to make at least one circular incision on the cornea of the eye of a patient and comprising an external tubular support forming a casing, having an axis and provided with a base portion for application thereof to the eye, an internal blade carrier which is movable in the support, and drive means for driving the blade carrier with respect to the support.

According to the invention, the blade carrier comprises a body which is coaxial to the support and which at its front portion carries a cylindrical blade which is also coaxial to the support and the cutting blade portion of which is formed by its lower circular edge, said drive means comprise means for driving the body in rotation with respect to the support about the axis, and means are provided for combining with said rotary movement a translatory movement of the body with respect to the support parallel to the axis in the direction of resulting in projection or in the direction of retraction of the cutting blade portion with respect to the base portion.

Advantageously, means are provided for preventing said translatory movement while permitting said rotary movement when the body reaches a predetermined position with respect to the support, in said translatory movement in said direction of resulting in projection, means preferably being provided for adjusting said predetermined position as desired.

In accordance with a preferred embodiment, the body is provided on its external surface with a screwthread co-operating with an internal screwthread carried by the support, and said drive means are in direct engagement with the body; in that case, advantageously, the internal screwthread is carried by an element which is rotatable about the axis in the support, between two abutments which are angularly spaced apart by a predetermined angle, and means are provided between the body and said element on the one hand and between said element and the support on the other hand, so that the frictional forces tending to oppose rotary movement of the blade carrier with respect to said element are different from the frictional forces tending to oppose rotary movement of said element with respect to the support; or again, said internal screwthread is carried by an element which is movable about the axis in the support, and means are provided between the body and said element on the one hand and between said element and the support on the other hand, so that the frictional forces tending to oppose the rotary movement of the blade carrier with respect to said element are less than the frictional forces tending to oppose the rotary movement of said element with respect to the support and that said element is nonetheless capable of rotary movement with respect to the support, when the body is driven in rotation in the direction of resulting in projection of the blade, but is immobilised with respect to the support when the body is driven in rotation in the opposite direction.

Preferably, the support and the blade carrier are each provided with a first and a second abutment, the first abutments being fixedly carried by the support and the blade carrier so as to form a limit in regard to retraction of the blade carrier into the support, when the said first abutments come into abutment, one of the second abutments being fixedly carried by one of the members (support or blade carrier) while the other of the second abutments is adjustably carried by the other member, so that, when they come into mutual contact, they form an adjustable limit to the movement of the blade carrier with respect to the support in the direction of the eye, said limit corresponding to the depth of the incision to be produced, while a display device for displaying the position of said abutment with respect to the member, which comprises an index and a scale expressed in units of depth of incision, is associated with said member and adjustable abutment.

In this respect, a preferred embodiment provides that said other member is the blade carrier which is provided with a second screwthread and a notched ring which is fixed with respect thereto, while the adjustable abutment comprises a shoulder of a screwthread sleeve member, co-operating with said second screwthread, and provided with a resilient pawl member, co-operating with said notched ring.

In addition, the scale of the display device referred to above is carried by the projections of the notched ring while the end of said pawl member defines, with the end of a mask or cover portion which is fixed with respect to the sleeve member, a window or opening for reading said scale forming said index.

In accordance with another feature of the invention, the support is provided with a fixed wall which is internal to the body of the blade carrier, forming a fixing element for a removable lens, which may be completed by an annular lens which is interposed between the blade and the support.

Finally, the base portion of the support is removable and the blade is interchangeable.

BRIEF DESCRIPTION OF THE DRAWING

The invention will be better appreciated from the following description given by way of purely illustrative and non-limiting example, and which will better show other advantages and features.

Reference is made to the accompanying drawings in which:

FIG. 1 is a general view of an embodiment of a trephine according to the invention, in section along a plane including the axis thereof, FIGS. 2 and 3 show a blade used in the invention, FIG. 2 being a view in section along a plane including the axis, such as plane II—II in FIG. 3, and FIG. 3 showing a plan view along the axis, FIGS. 4, 5 and 6 show the nut for locking the blade according to the invention, FIG. 4 being a view from below along the axis, FIG. 5 being a view in section along a plane including the axis, such as plane V—V in FIG. 4, and FIG. 6 being a side elevation, FIGS. 7 and 8 show the sleeve member for adjusting the depth of incision, FIG. 7 being a view from below along the axis and FIG. 8 being a view in section along the two half-planes marked at VIII—VIII in FIG. 7, FIGS. 9 and 10 show the toothed or notched locking and incision depth display ring co-operating with the sleeve member of FIGS. 7 and 8, FIG. 9 being a view taken along the axis and FIG. 10 being a side elevation, FIG. 11 is a diagrammatic view of an alternative embodiment of a detail of the invention, in section taken along a plane including the axis, FIG. 12 shows a view similar to that of FIG. 1 showing part of an alternative embodiment of the invention, FIG. 13 shows a view in section taken along line XIII—XIII in FIG. 12, and FIG. 14 is a diagrammatic view of a detail from FIG. 13.

DESCRIPTION OF THE PREFERRED EMBODIMENTS

Referring firstly to FIG. 1, shown therein is a trephine which comprises an external support 1 comprising a rear portion 1a of substantially cylindrical shape and a base portion 1b of substantially conical shape, which is screwed and centered on the portion 1a. The support is hollow and has a longitudinal axis 2. The portion 1b is open at 3. The opening 3 is bordered by a front face 4 forming a substantially spherical ring for resting on the eye of a patient, and is provided with a plurality of claws 5 which are of sufficient dimensions to prevent the trephine from slipping on the eye, while however being sufficiently small so as not to mark the eye; in an alternative form, the claws are circumferentially distributed at a spacing compatible with the number of stitch points to be formed when the graft is set in place, and are of dimensions such that they form on the eye marks which indicate the points at which stitching is to be done.

The rearward portion 1a of the support 1 is laterally provided with a bearing means 6 in which a rod 7 parallel to the axis 2 is capable of rotating. At one of its ends, the rod 7 carries a pinion 8 while its other end is provided with a conical bevel pinion 8a engaged with a similar pinion 8b which is fixed to the lower end of a rod 7a which is preferably inclined with respect to the axis 2 and which is capable of rotating in a second lateral bearing means 6a on the rearward portion 1a of the support 1; the other end of the rod 7a is provided with a manual operating knob or button 9 which is non-rotatably fixed on the rod 7a by means of a pin 10. The knob or button 9 is capable of sliding along the rod 7a and being guided in its sliding movement by slots 11 in which the ends of the pin 10 can move. A spring 12 tends to urge the button or knob 9 downwardly. At its lower part, the knob or button 9 has a portion 9a with lateral sides or flats. When the portion 9a is in the position shown in the drawing, it is positioned and held under the effect of the spring 12 in a housing or recess in the bearing means 6a, in which it can rotate. The housing has an upper opening 13 which is complementary in shape to the portion 9a so as to permit the portion 9a to pass through the opening 13 if it is in the proper angular position, when a pulling force is applied to the button 9 against the force of the spring 12. Beyond and on each side of the opening 13, the bearing means 6a terminates with an external face 14 in which there is a recess 15 which is also complementary in shape to the portion 9a but which is oriented perpendicularly to the opening 13 so as to receive the portion 9a in a position in which the portion 9a is locked against rotary movement and in which the pinion 8 can therefore no longer rotate. This locking effect can be removed at any moment by lifting the button or knob 9 against the force of the spring 12 and replacing the portion 9a in the housing disposed below the opening 13, in which that portion 9a can freely rotate. It will be noted that, in the housing, below the portion 9a, there is a lining member 16 which ensures minimum friction in regard to the knob 9 when it is rotated; likewise, interposed between the bearing means 6a and the pinion 8b and between the bearing means 6 and the pinions 8a and 8 are lining members indicated at 16a, 16b and 16c respectively which ensure minimum friction and which, in the case of the lining members 16b and 16c, ensure that the rod 7 is sealed with respect to the bearing means 6.

In an alternative embodiment which is not illustrated, the rod 7a further carries a pinion which is capable of engaging with the output pinion of a motor-reducing assembly, for example of the stepping forward movement type, to permit the trephine to be motorised; in that case, the motor may advantageously be controlled and/or monitored by a micro-processor which displays at any moment a value in respect of the descent movement of the cutting edge of the blade, or the depth of incision reached.

Placed within the rearward portion 1a of the support is an annular ring 17 which can rotate therein. The ring 17 is axially secured in the support by two ball-bearing assemblies 18 and 19 which may be replaced or completed by surfaces with a low coefficient of friction; in particular, portions of a toric ring of a material such as PTFE may be interposed between the respective balls of the bearing assemblies 18 and 19, the toric ring portions joining the adjacent balls in pairs so as to prevent dust capable of preventing rolling movement of the balls from penetrating between the balls. The ring 17 has an external surface 17a from which there radially projects a radial pin or projection 20 of small width. Moreover, the portion 1a of the support has a pin or projection 21 which projects inwardly towards the external surface 17a, to serve as an abutment in relation to the pin or projection 20. In this way, rotary movement of the ring 17 in the support is limited to an extent which is a little less than 360°. The ring 17 also carries an internal screwthread 22.

The screwthread 22 is intended to receive an external screwthread 24 provided on the body 23 of a blade carrier. The general shape of the blade carrier is conical, so as to correspond to the general shape of the support. In its rearward or upper portion, the body 23 is provided with a toothed ring 25 which engages with the above-mentioned pinion 8. The lower or front portion of the body 23 comprises a transverse face 26 which forms a support surface for a blade 27 which is substantially cylindrical and rotationally symmetrical about the axis 2 and which is held to the blade carrier by means of a locking and centering nut 28 having a screwthread by means of which it is screwed on to a screwthread on the blade carrier; advantageously, an arrow engraved on the outside of the nut 6 indicates the direction of rotation for screwing it tighter (see FIG. 6).

FIGS. 2 and 3 show an embodiment of the blade according to the invention, while FIGS. 4, 5 and 6 show in detail the nut for locking the blade on the above-mentioned support surface 26. It will be seen from these Figures that the blade 27 has a wall 59 which is substantially cylindrical and rotationally symmetrical and which terminates with a circular cutting edge 58 defining the cutting blade portion of the blade, and a rearward shoulder 29 which is defined by a plurality of regularly distributed radial arm portions, there being three such arm portions in this case. The ends of the arm portions are rounded and are disposed on the same imaginary circle 30. It will also be noted that there are openings or slots 31 which pass radially through the cylindrical wall 59 of the blade. Blades of different dimensions, depending in particular on the geometrical characteristics of the eye to be treated, may be readily fixed to the trephine according to the invention. For example, the diameter d of the cutting edge 58 may vary between 7 and 9.5 mm, with a pitch of 0.25 mm, the cut-out configuration of the shoulder 29 being identical from one blade to another.

By providing the blades with complementary screwthreads or suitable mutual engagement means, it would also be possible for two blades to be arranged concentrically, one within the other, in perfectly predetermined relative positions more particularly in respect of the cutting edges thereof, so that two concentric circular incisions may be made at the same time on the eye, in refractive surgery.

The nut 28 has a lower face 32 having a cut-out portion or configuration which is substantially or approximately complementary to that of the shoulder 29 of the blade so as to permit the shoulder 29 to be introduced into an internal cylindrical housing 33 in the nut 28. The diameter of the housing 33 is equal to the diameter of the circle 30, whereby, by tightening the nut, the cut-out portion thereof may be displaced with respect to that of the shoulder 29 of the blade, and the shoulder may be clamped against the face 26 (which will preferably have a light facing of complementary shape to the shape of the shoulder 29, to retain the blade against rotary movement when the nut is tightened). The cylindrical peripheral surface of the housing 33 serves at the same time as a means for centering the nut on the body 23, that is to say, with respect to the axis 2.

Moreover, at the location of its screwthread, the nut 28 has a recessed or apertured portion 34 whose edges are angularly spaced at about 100° to 120° and co-operate with a radial pin or projection 35 (FIG. 1) carried by the body 23. It will be appreciated that the pin or projection 35 is set in place after the nut has been so adjusted that the partial rotary movement permitted by the nut permits the blade to be tightened and released and removed through the cut-out configuration of the nut. This arrangement means that the nut 28 cannot be dismantled, and facilitates setting the blade in position. External notches or slots 36 on the nut permit it to be operated by means of a key or spanner designed for that purpose.

Returning now to FIG. 1, it will be seen that, between the ring 25 and the surface 26 of the body 23 of the blade carrier, the latter is provided with a sleeve member 37 having an internal screwthread by means of which it is screwed on to a screwthread 38 of the body 23. The sleeve member 37 which is seen from below in FIG. 7 and in section in FIG. 8 comprises an upper collar portion 37a and a lower pawl member 37b which is a curved resilient arm cut in a skirt portion 37c which extends the sleeve member in its lower part. The arm has an internal radial protrusion 39 which co-operates with the notches or slots of a notched or toothed ring 40 which is fixed with respect to the blade carrier (being made integrally therewith or produced separately and fitted thereto). The ring is shown in detail in FIGS. 9 and 10. Between its notches 41, it has projections 42 which carry reference marks 43 indicating the depth of incision for example in tenths and half-tenths of a millimeter.

The skirt portion 37c of the sleeve member 37, with the pawl 37b defines a window or aperture 44 (see FIG. 7) in which only a single one of the reference markings 43 appears, corresponding to the desired depth of incision.

It will also be seen from FIG. 1 that the support 1 has an internal wall 45 coupled to the portion 1a has by means of fixing elements 46 (pins or studs). The internal wall 45 on the one hand forms the upper rolling track 18a for the balls 18, and on the other hand comprises a shoulder 45a which is provided opposite a shoulder 23a of the blade carrier thereby to form fixed abutments for limiting the retraction movement of the blade carrier into the support; finally, it is internally screwthread at its front end 45b to receive a lens-carrier member 47.

Advantageously, interposed between the shoulders 45a and 23a is a ring 56 of a material with a low coefficient of friction such as a split ring of PTFE, in order to ensure that the body 23, in the limit position of retraction movement, does not jam against the wall 45 by friction between the shoulders 45a and 23a.

The limit position in respect of retraction movement of the body 23 with respect to the wall 45 and the portion 1a of the trephine may also be defined, as a complement to or as a substition for the shoulders 45a and 23a coming into abutment against each other, if appropriate by way of the ring 56, by one of the teeth of the ring 25 of the body 23, which is extended above said ring (with respect to the other teeth) coming into contact with a projecting pin or stud 57 which is carried by the wall 45 and which projects radially outwardly with respect to the wall, over the line of movement which the above-mentioned tooth is obliged to follow when the body 23 moves into its limit retraction position; the distance, measured parallel to the axis 2, by which the tooth 45 is thus extended with respect to the other teeth of the ring 25, is less than the pitch of the screwthread 22 and the screwthread 24 so that, after the body 23 has performed one revolution with respect to the ring 17 from the limit retraction position which is so defined, the extended tooth misses the projection 57 and does not prevent the descent movement of the body 23.

In the left-hand part of FIG. 1, the lens carrier member 47 carries a conical lens 48 which virtually completely fills the internal space defined by the wall 45. The lens 48 which is permanently connected to the member 47 by adhesive or the like, has a front extension portion 48a of smaller diameter, which is coaxial with the blade and disposed within the blade, and which is terminated by a concave surface 48b. When the member 47 is screwed home into the end 45b, the surface 48b is disposed approximately or substantially in spherical alignment, within the blade, with the surface 4 of the base portion of the support, thereby at the same time as the base portion to fit to the surface of the eye. Notches or slots 48c in the lens permit it ti be fitted or removed by means of a key, In an alternative form (not shown in the drawing), the arrangement will be such that the member 47 encases the lens 48 as far as its upper portion, in which case the above-mentioned slots or notches are provided in the upper end of the member 47 which is thus extended.

The right-hand part of FIG. 1 shows a view in section of another type of lens 49 which is fixed with respect to a member 47' similar to the member 47. The lens 49 has a central opening 50 which, being surrounded by a front surface 49b which is identical in respect of curvature and position to the surface 48b referred to above, makes it possible to carry out operations on nonspherical corneas, which for example have a cone deformation. This lens has two wires or threads 49a which cross in the centre of the opening 50 to form a centering reticle.

It will be seen therefore that, in the trephine according to the invention, the lens 48-49 is fixed with respect to the support 1.

Advantageously, as illustrated, the front extension portion 48a of the lens 48 (or the similar extension portion of the lens 49) is connected to the upper portion of the lens by a face 48d which is oriented approximately transversely with respect to the axis 2 and which is directed downwardly, that is to say, towards the blade 27, above the blade; in the embodiment illustrated, the face 48d has a frustoconical shape which is rotationally symmetrical about the axis 2, with the apex of the conical shape being directed downwardly, to facilitate the discharge of air when, when using a lens of the type illustrated at 47 in the left-hand part of FIG. 1, that is to say, a lens which does not have a central opening as indicated at 50 and which consequently defines a closed volume with the support 1 and the internal wall 45 of the trephine on the one hand and the eye of the patient on the other hand, a depression is formed within the trephine, relative to the exterior, by means of arrangements which will be described hereinafter; however, the face 48 could be of other shapes, for example a flat shape or a concave shape similar to that of the face 48b.

In a complementary fashion, when the outside diameter of the cylindrical wall 59 of the blade 27 is sufficiently smaller than the inside diameter of the annular surface 4, which defines the minimum inside diameter of the portion 1b, it is advantageous to provide, between the cylindrical wall 59 and the internal cylindrical surface 60 of the portion 1b which is adjacent to the surface 4 thereof, an annular lens 61 which is fixed with respect to the portion 1b and which is thus disposed opposite the face 48d of the lens 48 (or the corresponding part of the lens 49), by way of spaces 62 between the cylindrical wall 59 of the blade, the radial arms defining the shoulder 29 thereof, and the periphery of the cut-out portion of the face 32 of the nut 28; the operator thus enjoys total visibility in regard to the cornea of the patient, including at the outside of the circular blade.

Outwardly, that is to say, towards the cornea, the annular lens 61 advantageously has a concave surface 61a which extends the surface 48b of the lens 48 as far as the surface 4 so as to be supported on the eye at the same time as those surfaces, and fitting thereto; inwardly of the trephine, it may have a flat surface 61b which is perpendicular to the axis 2 as illustrated, which permits the assembly formed by the lens 48 (or 49) and the lens 61 to provide two different degrees of enlargement respectively for the inside and the outside of the circular blade, or a surface having a shape which is complementary to that of the surface 48d, to provide uniform enlargement.

Finally, it will be noted that the support 1 is provided with connecting tip members 51 (there are two, of which only one can be seen in the drawing) for connecting the internal space in the trephine (between walls 45 and walls 1a and 1b), on the one hand to a fluid source and on the other hand to a suction source for generating a partial vacuum in the field of operation, in order thereby to apply the trephine against the eye and to give best immobilisation thereof, and a circulation of aseptic fluid in the field of operation, when using a non-apertured lens of the type illustrated for example at 48 in the left-hand part of FIG. 1; producing the reduced pressure and the circulation of fluid in the above-indicated manners is facilitated by a suitable configuration in respect of the space inside the trephine.

Advantageously, in this case, a microprocessor continuously monitors and pilots the pressure obtaining within the trephine in order to detect the presence of any air bubbles and to provide for elimination thereof.

Advantageously, in the case of the preferred embodiment illustrated, the respective refractive indices of the lenses 48 and 61 are different, being lower for the main lens 48 and higher for the lens 61; by way of nonlimiting example, the lens 48 may have a refractive index of the order of from 140 to 150, while the lens 61 may have a refractive index of the order of 180.

In an alternative form of a detail as shown diagrammatically in FIG. 11, claws 5' of the type referred to hereinbefore, which are intended to form marks on the eye for indicating the positioning of the sutures, are supported by a ring or disc 5a which can slide freely in the nose portion 1b of the support 1. A ring or disc 52 is screwed into the nose portion of the support, with a substantial pitch (2.5 to 3 mm) and is connected by means of pins 53 through openings 54 in the portion 1b to an external operating ring 55. When the ring 55 is raised (by unscrewing the disc 52), a space is made available above the disc 5a and, upon coming into contact with the eye, the claws 5' may rise and be retracted into the surface 4. By rotating the ring 55 for example through a quarter of a turn, the claws are caused to project by from 6 to 7 tenths of a millimeter and they are held engaged in the eye under the action of the disc 52.

The mode of operation of the trephine according to the invention will now be described. It will be assumed that the initial and definitive adjustments have been made at the moment of assembly of the apparatus. These adjustments are to give the following results:

when the surface 45a and the surface 23a are in contact by way of the ring 56 and/or the extended tooth of the ring 25 is in contact with the abutment 57, the cutting edge of the blade is within the trephine, inwardly of the surface 4, 48b or 49b, 61a;

when the display provided by means of the screwthreaded sleeve member 37 and the notched ring 40 is or corresponds to zero, the blade carrier 23 can descend only until the cutting edge of the blade is contained within the surface 4, 61a, 48b or 49b.

The operator has placed the blade 27 on the surface 26 of the blade carrier 23 and has locked it in that position by means of the nut 28. This operation was possible only after the portion 1b of the support had been withdrawn from the portion 1a. In order to produce the locking effect, the operator will have used a key or spanner which acts on the notches or slots 36 of the nut 28, with the knob or button 9 having been first placed in its position for total blocking or locking of the apparatus.

He then acts on the sleeve member 37, screwing it (or unscrewing it) on the body 23 until the desired depth of incision occurs in the window or aperture. This rotary movement can be effected because the pawl member 37b, which is flexible, jumps from one notch to another in the toothed ring 40, sliding over the sloping surfaces thereof (irrespective of the direction of rotation). When these adjustments have been made, the portion 1b is screwed back on to the portion 1a. It will be noted (see FIG. 1) that the back of the pawl member 37b is then very close to an internal cylindrical surface of the portion 1b, which prevents the pawl member from coming completely out of the notch at which it was set, under the effect of a force tending to cause relative rotation of the body 23 and the sleeve member 37. The sleeve member 37 is in this way completely non-rotatably fixed with respect to the blade carrier.

It will have been noted that, when this adjustment operation is performed, the axial height of the shoulder 37a of the sleeve member 37 is actually fixed with respect to the body 23. Now, it should be observed that the shoulder 37a is capable of bearing on an internal radial annular extension portion 17b of the ring 17 mounted rotatably in the support. When that bearing condition is achieved, the limit in respect of the descent movement of the body 23 with respect to the support 1 has been reached. It will be seen therefore that, the more the collar portion or shoulder 37a is moved downwardly with respect to the body 23, the quicker that limit will be reached and therefore the shorter will be the extent by which the blade projects from the support. Therefore, the position of the sleeve member 37 on the body 23 is properly related to the depth of incision to be produced.

The operator then unlocks the button or knob 9 and manually actuates the pinion 8 in order to raise the body 23 again. Rotation of the pinion 8 causes rotation of the ring 25 and therefore rotation of the body 23. The friction forces which naturally occur at the screwthreads 22 and 24 tend to transmit the rotary movement to the ring 17 which is mounted on axial bearing assemblies, the frictional resistance of which is substantially lower than that of the screwthreads. If however that is not the case naturally, then this hierarchy will be respected by the provision of a brake means between the body 23 and the ring 17 of the nut brake or check means type (not shown), which is for example in the form of a resilient blade portion which bears by virtue of curvature against the threads 24 of the body 23. If the abutments 20 and 21 cooperate to prevent rotary movement of the ring 17, the body 23 is unscrewed and rises, entraining the blade 27 into the support, until the surfaces 45a and 23a are in contact. The knob or button 9 can then be re-locked.

The surgeon then places the trephine on the eye on which the operation is to be performed, and proceeds to centre the trephine by means of a marker provided for that purpose on the lens 48 or the reticle of the lens 49. In the design having retractible claws 5', the surgeon will set the trephine in position, after the claws have been retracted. By virtue of these means, the trephine can be set in position with a very high degree of precision, the lens being a fixed component of the trephine and resting directly on the eye. The trephine is then gripped to the surface of the eye by its claws 5 or 5'. The interrelation between the trephine and the eye is strengthened and enhanced by setting in operation the suction-irrigation device which extracts the air from the closed space formed by the blade carrier, the support 1 and the eye, and replaces it by a physiological serum.

The button or knob 9 is then operated, to cause the descent movement of the blade carrier. It should be noted in this connection that the rotary movement of the pinion 8 firstly causes rotary movement of the body 23 and the ring 17 together, by the friction between the screwthreads, over a little less than 360°, in respect of the toothed wheel 25. The abutments 20 and 21 are then again in contact, by way of their other faces, and continuing rotation of the knob 9 causes the body 23 to be screwed into the ring 17. The blade 27 rotates and descends, reaches the eye, and makes an incision in the cornea. During this operation, the circulating serum passes between the lens and the cutting blade portion by way of openings 31 in the blade and entrains anything which could detrimentally affect supervision of the operation (blood, debris, etc) through the lens and the microscope which is disposed therebehind. The relative downward movement of the blade is stopped by contact of the collar portion 37a and the internal radial extension portion 17b of the ring 17. The selected depth of incision has then been reached.

The surgeon then rotates the knob or button 9 in the opposite direction, which results in rotary movement of the blade 27 but without upward movement since, at that moment, the ring 17 turns at the same time as the body 23. This rotation is also over a little less than 360° and stops when the abutments 20 and 21 again come into a condition of co-operation. This rotary movement made it possible to equalise the depth of the incision over the entire periphery thereof, while releasing the torsional and shearing stresses to which the cornea was subjected during the cutting operation. The blade is then raised by continuing the rotation of the knob or button 9 in the same direction as far as the travel-limit abutment 45a, 23a, 56 and/or 25, 57.

In an alternative form (not shown), in contrast to the described embodiment, the arrangement is such as to make the contact between the threads 22 and 24 as smooth and gentle as possible, with a brake means being positioned between the ring 17 and the portion 1a of the support 1, so that the frictional forces of the ring 17 on the portion 1b are greater than those of the body 23 on the ring 17. Thus, in the operation of moving the blade downwardly, actuation of the knob 9 will first permit the blade to be moved downwardly as far as the required depth and then, by rotary movement of the knob in the same direction, cause the ring 17 to be rotated, without downward movement of the blade. It will be seen that, in this alternative form, the incision is made and finished by rotation of the knob 9 in the same direction. This arrangement may have an advantage insofar as it gives a small degree of simplification in handling, which avoids the possibility of withdrawing the trephine before the operation has been completely concluded, as may occur in the embodiment described above.

In conclusion, fairly different levels of friction as between the members 23 and 17 and 17 and 1b should be provided so as to produce a sequence in regard to producing the rotary descent motion and the rotary movement without descent. The choice as to the location at which the higher level of friction will be provided will depend on the order of the sequence which is to be produced.

More generally, any suitable means may be used in order for the frictional forces tending to oppose the rotary movement of the member 23 with respect to the member 17 to differ from the frictional forces tending to oppose the rotary movement of the member 17 with respect to the support 1, in order to produce such a sequence as referred to above.

Thus, FIGS. 12 to 14 which bear the same references as the previous Figures, to denote similar members or portions, illustrate an alternative embodiment in which the abutments 20, 21, 57 are eliminated and the ball bearing assemblies 18 and 19 are replaced by surfaces with a low coefficient of friction; any other method of axially immobilising the annular ring 17 in the support 1, while allowing the possibility of relative rotation about the axis 2, may be selected within the scope of this alternative embodiment, as in regard to the embodiments described hereinbefore.

In this alternative embodiment, the peripheral surface 17a with which the ring 17 faces away from the axis 2 is cylindrical and rotationally symmetrical about the axis, and, facing the peripheral surface 17a, the portion 1a of the support 1 has a surface 1c which is directed towards the axis 2 and which is also cylindrical and rotationally symmetrical thereabout, while being larger in diameter than the surface 17a.

Interposed between the surfaces 1c and 17a is an intermediate ring 63 having an external peripheral surface 63a which is cylindrical and rotationally symmetrical about the axis 2 and whose diameter is substantially identical to the diameter of the surface 1c of the support 1, with which it is in contact, while permitting relative rotation, the frictional forces tending to oppose such rotation being greater than the frictional forces tending to oppose rotation of the body 23 of the blade carrier with respect to the ring 17, at the screwthreads 24 and 22; for example, the intermediate ring 63 is split at 64 and force-fitted into the portion 1a of the support, so that its surface 63a is pre-stressed into intimate contact with the surface 1c of the portion 1a.

Facing the surface 17a of the ring 17, the intermediate ring 63 has an internal peripheral surface 63b which is cylindrical and rotationally symmetrical about the axis 2 and whose diameter is preferably substantially larger than the diameter of the surface 17a, in order to permit relative free rotary movement.

Moreover, the intermediate ring 63 is mounted freely between the surfaces with a low coefficient of friction, which, in this embodiment, replace the respective rolling surfaces, on the support 1, for the balls 19 and 20, in the embodiment illustrated in FIG. 1.

The ring 63 has radial openings extending entirely therethrough, at regularly angularly spaced positions, to serve as housings for balls, the diameter of which is greater than the thickness of the ring 63.

One of the housings is advantageously formed by the slot 64; in the illustrated embodiment, two openings 64a and 64b are also provided, with the three openings 64, 64a, and 64b being disposed at relative angular spacings of 120°, and receiving one ball each opening, the balls being indicated at 65, 65a and 65b respectively and being freely mounted.

Within the ring 17, each of the balls is received in a slot or notch 66, 66a and 66b respectively, in the external cylindrical surface 17a.

The notches are identical and, when seen in section along a transverse plane with respect to the axis 2, as shown in particular in FIGS. 13 and 14, are of an approximately triangular shape defined by two flat surfaces which are parallel to the axis 2 and which are for example substantially or approximately perpendicular to each other and one of which, being disposed at an upstream position if reference is made to a predetermined direction 67 of rotation of the body 23 of the blade carrier with respect to the support 1 in the direction of descent movement of the blade towards the eye of the patient, is disposed entirely downstream of a plane joining the axis 2 to its junction with the surface 17a of the ring 17, forming with said plane a dihedron with an angle $\beta$ which is less than 90° but more than 0°, while the other said surface, which is disposed downstream of the first surface, is disposed entirely upstream of a plane joining the axis 2 to its junction with the surface 17a of the ring 17, forming with said plane a dihedron of angle $\gamma$ which is more than 90° but less than 180°.

The dimensions of the notches are such that, when the corresponding ball is engaged into such a notch to the maximum extent, that ball projects with respect to the surface 17a and has, within the corresponding opening of the intermediate ring 63, a region which is disposed in the immediate vicinity of the surface 1c of the portion 1a of the support, without however coming into contact with said surface 1a.

When the body 23 of the blade carrier is driven in rotation in direction 67, in particular from an initial position thereof, in which it is in the limit position in respect of retraction of the blade, as defined by the co-operation of the surfaces 23a and 45a, the balls tend precisely to occupy that position because the frictional forces at the screwthreads 22 and 24 tend to cause rotation of the ring 17 jointly with the body 67 while higher frictional forces occurring at the location of the surfaces 63a and 1c which are in contact tend to oppose the rotary movement of the ring 17, which causes each ball to move into a position of abutment, on the one hand in a downstream direction, against the downstream surface of the corresponding opening in the ring 63 (except possibly as regards the opening defined by the slot 64, if reference is made to the illustrated example in which the slot has larger dimensions than the openings 64a and 64b, in the peripheral direction), and, on the other hand, in an upstream direction, against the upstream surface of corresponding notch of the ring 17.

As soon as that condition is reached, the descent movement of the body 23 and the blade begins, by rotation of the body 23 in the ring, which remains immobile with respect to the support 1 because the frictional forces opposing rotary movement thereof are higher than the frictional forces opposing rotary movement of the body 23 within the ring.

When the displayed depth of incision is reached, the shoulder 37a of the sleeve member 37 comes into a condition of abutment against the shoulder 17b of the ring 17 and continued driving of the body 23 with a rotary movement in the direction 67 accordingly causes joint rotation of the ring 17 and the ring 63 by way of the balls 65a and 65b which are in a condition of abutment, with friction of the surface 63a thereof against the surface 1c of the portion 1a of the support; consequently, in this embodiment, rotary movement of the blade without descent movement is produced by driving the body 23 of the blade carrier in the same direction as in the descent movement, by using a slightly higher force since the rotary movement of the ring 63 with respect to the support 1 then replaces rotary movement of the body 23 with respect to the ring 17.

It will be noted that the angle of rotation without descent movement of the blade is not limited in this case.

When the operator wishes to retract the blade, he reverses the direction of rotation of the body 23 which, by virtue of the friction between the screwthreads 24 and 22 on the one hand and the shoulders 37a and 17b on the other hand, also tends to drive the ring 17 in the opposite direction to the direction indicated by arrow 67; each ball 65, 65a and 65b is then urged outwardly by a cam effect which is applied thereto by the surface of the corresponding notch, which is disposed at a downstream position, when referring to direction 67, and accordingly is pressed into contact with the surface 1c of the portion 1a of the support 1.

FIG. 14 diagrammatically shows the break-down of the forces which are then involved at the ball 65, an identical phenomenon occuring at the balls 65a and 65b.

$\alpha$ denotes the angle formed by said downstream surface of the notch 66 (when referring to direction 67) with a tangent to the surface 1c at the point of contact of the ball with that surface.

F denotes the force applied to the ball 65 by the ring 17, by way of the notch 66, along the line bisecting the angle $\alpha$.

This force results in identical forces N respectively applied perpendicularly to the surface 1a (that is to say, radially) at the point of contact of the ball 65 therewith, and perpendicularly to said downstream surface of the notch 66 (when referring to direction 67). It is shown that:

$$N \simeq F/\sin \alpha$$

The first of the above-indicated forces N results in a frictional force N.f in respect of the ball 65 against the surface 1c, wherein f denotes a coefficient of friction.

By selecting a suitable angle $\alpha$, for example of the order of 10° in the illustrated embodiment, the result is that, when the body 23 begins to be driven in rotation in the opposite direction to the direction 67, sufficient frictional forces thus occur between the balls 65, 65a, and 65b and the surface 1c, to immobilise the ring 17 with respect to the support 1, in spite of the forces that may be applied thereto by friction by the body 23, by way in particular of the shoulders 37a and 17b, which makes it possible to translate the rotary movement of the body 23 immediately by the upward movement of the blade in the support 1 towards the limit retraction position.

The trephine according to the present invention makes it possible to combine optimum conditions for achieving good trephination of the cornea. In fact, adjustment in respect of the depth of incision is made before the apparatus is set in position, thereby eliminating a large number of faulty settings and disorders of adjustment in the course of operation. The depth of the incision may be for example set to 0 to 1.2 mm, in steps of 5 hundredths of a millimeter. Accordingly, it is possible to carry out lamellar trephination operations, even deep operations, as the depth of the incision is uniform by virtue of the rotary movement without axial movement at the end of the operation.

The trephine according to the invention makes it possible readily to centre and fix the trephine properly on the eye, while its claws and its suction-irrigation system prevent any slipping, which would cause a double incision. In addition, the above-mentioned system guarantees proper placing of the eye on the front surface of the trephine and therefore ensures that the incision made is always vertical. It also makes it possible to remove blood if the cornea is vascularised, thereby avoiding interference in the field of vision of the operator, and to avoid damaging the iris and the crystalline lens, in the case of a perforating incision. It will also be recalled that the marks left by the claws mark the sutures to be made and consequently may form initial or pilot holes which are properly perpendicular to the surface of the eye over the major part of the thickness through which the suture thread passes, thereby reducing the tendency of the suture thread to cause local incision in the edges of the openings through which the thread passes, which result in a reduction in the tension of the suture thread.

It will also be noted that the blades, besides being disposable, are interchangeable. Thus, a single trephine can be used to carry out trephination operations at different diameters (for example from 7 to 9.5 mm, in steps of 25 hundredths of a millimeter).

Finally, the lenses which are fixed to the trephine may be adapted to the shape of the sick eye (which has for example a keratoconus) and the trephine in its entirely can be sterilised in an autoclave.

The invention is therefore attractive in regard to use in the field of ophtalmological surgery.

The invention is not restricted to the description set out hereinbefore but in contrast covers all the variations which could be made therein without thereby departing from the spirit or scope of the invention.

What I claim as my invention is:

1. A trephine for making a circular incision in the cornea of an eye, said trephine comprising:
   (a) a tubular support having an axis and being provided with a base portion having a front surface for application to the eye,
   (b) a blade carrier coaxial with, and movable within, said support, said blade carrier having a front portion,
   (c) a cylindrical blade coaxial with said support mounted on the front portion of said blade carrier, said blade having a circular cutting edge,
   (d) drive means for simultaneously rotating and axially translating said blade carrier with respect to said support, the translatory movement serving to project the blade cutting edge from and retract it into the base portion of said support, and
   (e) means for preventing the translatory movement but permitting the rotary movement of said blade carrier, upon operation of said drive means, after the cutting edge of said blade reaches a predetermined location of projection from the base portion of said support,
   whereby the cutting edge of the blade can be rotated within an incision without being retracted from the incision or moving forward to deepen the incision.

2. A trephine according to claim 1 including means for selecting the predetermined location of projection of said blade cutting edge.

3. A trephine for making a circular incision in the cornea of an eye, said trephine comprising:
   (a) a tubular support having an axis and being provided with a base portion having a front surface for application to the eye,
   (b) a ring rotatable within said support about the axis thereof, said ring having a screw thread,
   (c) a blade carrier coaxial with said support, said blade carrier having a front portion, and said blade carrier having a screw thread cooperable with the screw thread of said ring,
   (d) a cylindrical blade coaxial with said support mounted on the front portion of said blade carrier, said blade having a circular cutting edge,
   (e) drive means for rotating said blade carrier with respect to said support, cooperation between the screw threads of the blade carrier and ring causing the blade carrier to be translated as it is rotated,
   (f) means for limiting the angle through which said ring can rotate with respect to said support, and
   (g) cooperable means carried by said ring and said blade carrier for limiting the translatory movement of said blade carrier in the direction which causes the blade cutting edge to project from the base portion of said support.

4. A trephine according to claim 3 including means for causing the frictional resistance to relative rotation between said support and said ring to be different from the frictional resistance to relative rotation between said ring and said blade carrier.

5. A trephine according to claim 3 including means for causing the frictional resistance to relative rotation between said support and said ring to be less than the frictional resistance to relative rotation between said ring and blade carrier.

6. A trephine according to claim 4 or 5 wherein said frictional resistance causing means includes smooth axially-facing abutments between said support and said ring.

7. A trephine according to claim 4 or 5 wherein said frictional resistance causing means includes rolling elements between said support and said ring.

8. A trephine according to claim 4 or 5 wherein said frictional resistance causing means includes brake means between said ring and said blade carrier.

9. A trephine according to claim 3 wherein said means for limiting the angle through which said ring can rotate includes a first abutment projecting from said ring and a second abutment projecting from said support, the second abutment being located in the path of movement of the first abutment as said ring rotates with respect to said support.

10. A trephine for making a circular incision in the cornea of an eye, said trephine comprising:
    (a) a tubular support having an axis and being provided with a base portion having a front surface for application to the eye,
    (b) a ring rotatable within said support about the axis thereof, said ring having a screw thread,
    (c) a blade carrier coaxial with said support, said blade carrier having a front portion, and said blade carrier having a screw thread cooperable with the screw thread of said ring,
    (d) a cylindrical blade coaxial with said support mounted on the front portion of said blade carrier, said blade having a circular cutting edge,
    (e) drive means for rotating said blade carrier with respect to said support, cooperation between the screw threads of the blade carrier and ring causing the blade carrier to be translated as it is rotated, and
    (f) cooperable means carried by said ring and said blade carrier for limiting the translatory movement of said blade carrier in the direction which causes the blade cutting edge to project from the base portion of said support.

11. A trephine according to claim 10 including means for causing the frictional resistance to relative rotation between said support and said ring to be different from the frictional resistance to relative rotation between said ring and said blade carrier.

12. A trephine according to claim 10 including means for causing the frictional resistance to relative rotation between said support and said ring to be less than the frictional resistance to relative rotation between said ring and blade carrier.

13. A trephine according to claim 11 or 12 wherein said frictional resistance causing means includes smooth axially-facing abutments between said support and said ring.

14. A trephine according to claim 11 or 12 wherein said frictional resistance causing means includes rolling elements between said support and said ring.

15. A trephine according to claim 11 or 12 wherein said frictional resistance causing means includes brake means between said ring and said blade carrier.

16. A trephine according to claim 11 or 12 wherein said frictional resistance causing means includes an intermediate ring between the external surface of said rotatable ring and the internal surface of said support, the external surface of said rotatable ring having at least one notch radially aligned with an opening and notch, said notch being so shaped that when said blade carrier rotates in a direction serving to retract the blade cutting edge into the support the ball is pressed radially outwardly against the internal surface of the support, thereby preventing relative rotation between the rotatable ring and the support, and when the blade carrier rotates in the opposite direction serving to project the blade cutting edge the ball moves radially inwardly away from the internal wall of the support, thereby permitting relative rotation between the rotatable ring and the support.

17. A trephine according to claim 1, 3 or 10 including cooperable abutment means carried by said support and blade carrier for limiting the translatory movement of said blade carrier in a direction which retracts the cutting edge of the blade into the base portion of the support.

18. A trephine according to claim 3 or 10 including a sleeve threadably engaging said blade carrier, so as to be rotatable and axially translatable with respect to said blade carrier, a notched ring fixed with respect to said blade carrier, and a pawl carried by said sleeve and cooperating with said notched ring, and wherein said cooperable means (g) includes an abutment carried by said ring and a cooperating abutment carried by said sleeve.

19. A trephine according to claim 18 including reference marks carried by the projections of said notched ring, and a window in said sleeve through which any one marking can be seen when said pawl is within a notch, thereby indicating the permissible amount of travel of the blade carrier in a direction for projecting the cutting edge of the blade from the base portion of the support.

20. A trephine according to claim 18 in which said base portion of said support is removable to uncover said sleeve and said base portion forms a radial external abutment means for holding said pawl means in its position.

21. A trephine according to claim 20 in which said removable lens is internally apertured.

22. A trephine according to claim 20 in which said removable lens has a centering marking means.

23. A trephine according to claim 1, 3 or 10 in which said support is provided with a fixed wall inwardly of said blade carrier, said fixed wall forming a means for mounting a removable lens having a front surface for facing the eye.

24. A trephine according to claim 23 in which said front surface of said lens is concave, and corresponds to the curvature of the eye to be treated.

25. A trephine according to claim 23 in which around said blade, said support carries an annular lens, opposite which said removable lens has a second front surface which is disposed inwardly in the trephine relative to said front surface of said removable lens, and means are provided on at least one of said blade and said blade carrier for permitting viewing of said annular lens through said second front surface of said removable lens.

26. A trephine according to claims 1, 3 or 10 in which said cylindrical blade is removably fixed to said front portion of said body of said blade carrier by means of a fixing and centering nut which is connected to said body.

27. A trephine according to claim 1, 3 or 10 in which said cylindrical blade is removably fixed to said front portion of said body of said blade carrier by means of a fixing and centering nut which is connected to said body.

28. A trephine according to claim 1, 3 or 10 in which said drive means comprise a pinion which is rotatably mounted in said support and which engages a toothed ring which is fixed with respect to said blade carrier, and means for imparting a rotary movement to said pinion as desired.

29. A trephine according to claim 28 in which said drive pinion is operatively connected to an actuating rod which is provided with a means for locking rotary movement thereof and thereby immobilizing said blade carrier.

30. A trephine according to claim 1, 3 or 10 in which said front surface of said base portion of said support is provided with claws which are circumferentially spaced at distances corresponding to the spacing between sutures to be made.

31. A trephine according to claim 30 in which said claws are retractible.

32. A trephine according to claim 1, 3 or 10 in which said front surface of said base portion of said support is provided with claws for preventing sliding thereof on the eye without marking the eye.

33. A trephine according to claim 1, 3 or 10 in which said support is provided with two connecting tip means which open into a space between said support and said blade carrier, for connecting said space to a fluid source and a suction source.

34. A trephine according to claim 1, 3 or 10 in which said blade has two circular concentric lower cutting edges in predetermined relative positions, each of which defines a cutting blade portion.

* * * * *